US00PP09843P

United States Patent [19]

Van Koeveringe

[11] Patent Number: Plant 9,843

[45] Date of Patent: Apr. 1, 1997

[54] CHRYSANTHEMUM PLANT NAMED 'SPRING DELANO'

[76] Inventor: John A. Van Koeveringe, 5th St., R.R. #3, St. Catherines, Ontario, Canada, L2R 6P9

[21] Appl. No.: 512,012

[22] Filed: Aug. 7, 1995

[51] Int. Cl.[6] ..... A01H 5/00

[52] U.S. Cl. ..... Plt./76

[58] Field of Search ..... Plt./76

[56] References Cited

U.S. PATENT DOCUMENTS

P.P. 8,345 10/1993 Vandenberg ..... Plt./82

*Primary Examiner*—Howard J. Locker
*Attorney, Agent, or Firm*—Foley & Lardner

[57] ABSTRACT

A Chrysanthemum plant named Spring Delano particularly characterized by its flat capitulum form; decorative capitulum type; red-purple ray floret color, with the base of the ray floret being white and variable in length depending on environmental conditions; diameter across face of capitulum of 110 to 127 mm when fully opened, when grown as a pinched disbudded pot mum; photoperiodic flowering response to short days of 55 to 63 days; plant height, with 14 long days after sticking unrooted cuttings and with 1 to 2 applications of 2500 ppm B-9 SP, ranges from 25 to 35 cm when grown as a pinched pot mum with 4 cuttings in a 15 cm pot; spreading and prolific branching pattern; and recommended as a disbudded pot mum.

1 Drawing Sheet

The present invention comprises a new and distinct cultivar of Chrysanthemum, botanically known as *Dendranthema grandiflora*, and referred to by the cultivar name Spring Delano.

Spring Delano, identified as 5405 (92-#02049), is a spontaneous mutation of the cultivar Delano, disclosed in U.S. Plant Pat. No. 6,950, and was selected to expand the color range of the parental variety.

Spring Delano was discovered and selected by inventor John A. Van Koeveringe as one flowering plant within a flowering block of Delano in March 1992, in a controlled environment in St. Catherines, Ontario, Canada.

The first act of asexual reproduction of Spring Delano was accomplished when vegetative cuttings were taken from the initial selection in May 1992 in a controlled environment in St. Catherines, Ontario, Canada, by John A. Van Koeveringe.

Horticultural examination of controlled flowerings of successive plantings has shown that the unique combination of characteristics as herein disclosed for Spring Delano are firmly fixed and are retained through successive generations of asexual reproduction.

Spring Delano has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and Leamington, Canada, under greenhouse conditions which approximate those generally used in commercial greenhouse practice.

The following traits have been repeatedly observed and are determined to be basic characteristics of Spring Delano, which, in combination, distinguish this Chrysanthemum as a new and distinct cultivar:

1. Flat capitulum form.
2. Decorative capitulum type.
3. Red-purple ray floret color, with the base of the ray floret being white. The length of the white base portion of the ray floret is variable, depending on environmental conditions.
4. Diameter across face of capitulum of 110 to 127 mm when fully opened, when grown as a pinched disbudded pot mum.

5. Photoperiodic flowering response to short days of 55 to 63 days.
6. Plant height, with 14 long days after sticking unrooted cuttings and with 1 to 2 applications of 2500 ppm B-9 SP, ranges from 25 to 35 cm when grown as a pinched pot mum with 4 cuttings in a 15 cm pot.
7. Spreading and prolific branching pattern.
8. Recommended as a disbudded pot mum.

The accompanying photographic drawing is a top perspective view of a potted mum of Spring Delano, with 4 cuttings in a 15 cm pot, with the colors being as nearly true as possible with illustrations of this type.

Of the commercial cultivars knows to the inventor, the most similar in comparison to Spring Delano is the parent cultivar Delano. All traits of Spring Delano are similar to those of Delano, except for the ray floret color. The ray floret color of Spring Delano is red-purple (R.H.S. 70A to 70B), with the base of the ray floret being white, while the ray floret color of Delano is a much redder dark red-purple (R.H.S. 60A to 60B).

In the following description color references are made to The Royal Horticultural Society Colour Chart. The color values were determined on plant material grown as a pinched disbudded pot mum in Salinas, Calif. on Aug. 29, 1994.

Classification:

*Botanical.*—*Dendranthema grandiflora* cv Spring Delano.

*Commercial.*—Flat decorative disbud pot mum.

INFLORESCENCE

A. Capitulum:

*Form.*—Flat.

*Type.*—Decorative.

*Diameter across face.*—110 to 127 mm when fully opened.

B. Corolla of ray florets:

*Color (general tonality from a distance of three meters).*—Red-purple, with base of ray floret being white. The length of the white base portion of the ray floret is variable, depending on environmental conditions.

*Color* (*upper surface*).—70A to 70B; base 155D.
*Color* (*under surface*).—78B to 78C; base 155D.
*Shape.*—Flat, oblong.

C. Corolla of disc florets:
*Color* (*mature*).—Closest to 154B.
*Color* (*immature*).—Closest to 144C.

D. Reproductive organs:
*Androecium.—Present on disc florets only; no pollen.*
*Gynoecium.*—Present on both ray and disc florets.

PLANT

A. General appearance:
*Height.*—25 to 35 cm when grown as a pinched pot mum with 14 long days after sticking unrooted cuttings prior to start of short days, with 1 to 2 applications of 2500 ppm B-9 SP.
*Branching pattern.*—Spreading and prolific.

B. Foliage:
*Color* (*upper surface*).—147A.
*Color* (*under surface*).—147B.
*Shape.*—Lobed and slightly serrated.

What is claimed is:

1. A new and distinct Chrysanthemum plant named Spring Delano as described and illustrated.

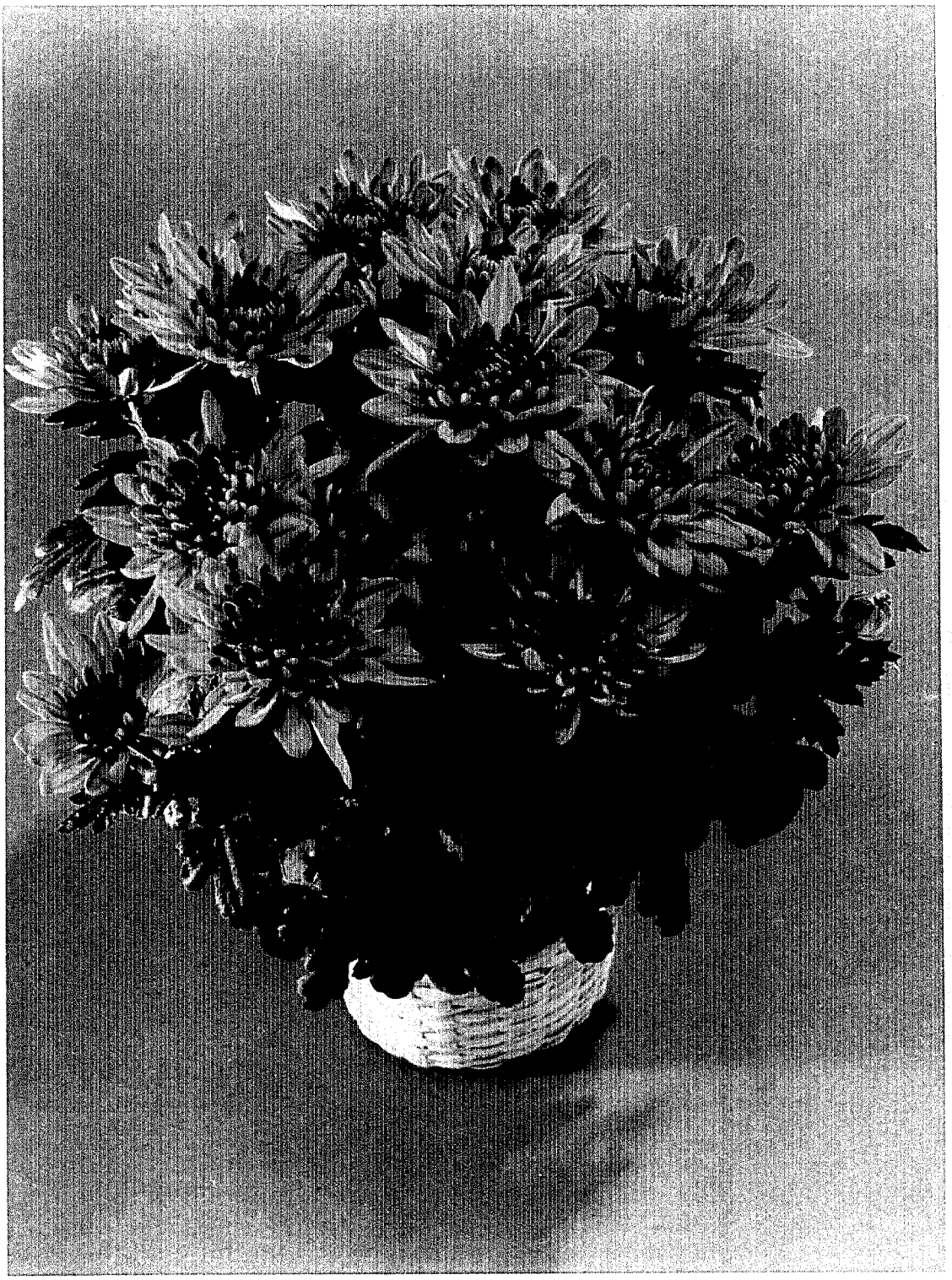

* * * * *